US00PP21634P2

(12) United States Plant Patent
Hayman

(10) Patent No.: US PP21,634 P2
(45) Date of Patent: Jan. 18, 2011

(54) ***EUONYMUS* PLANT NAMED 'HAYMAN'**

(50) Latin Name: *Euonymus alata*
Varietal Denomination: Hayman

(75) Inventor: Michael Hayman, Louisville, KY (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/653,202

(22) Filed: Dec. 9, 2009

(51) Int. Cl.
*A01H 5/00* (2006.01)

(52) U.S. Cl. ..... Plt./246
(58) Field of Classification Search ..... Plt./246

See application file for complete search history.

*Primary Examiner*—Kent L Bell
(74) *Attorney, Agent, or Firm*—C. A. Whealy

(57) ABSTRACT

A new and distinct cultivar of *Euonymus* plant named 'Hayman', characterized by its compact, upright and mounding plant habit; relatively rapid growth rate; freely branching habit; relatively small and fine leaves; and attractive autumn leaf color.

2 Drawing Sheets

Botanical designation: *Euonymus alata.*
Cultivar denomination: 'HAYMAN'.

BACKGROUND OF THE INVENTION

The present invention relates to a new and distinct cultivar of *Euonymus* plant, grown as an ornamental shrub, botanically known as *Euonymus alata* and hereinafter referred to by the name 'Hayman'.

The new *Euonymus* plant originated from an open-pollination during the autumn of 2000 of *Euonymus alata* 'Rudy Haag', not patented, as the female, or seed, parent with an unknown selection of *Euonymus alata* as the male, or pollen, parent. The new *Euonymus* plant was discovered and selected by the Inventor during the autumn of 2002 as a single plant within the progeny of the stated open-pollination in a controlled environment in Louisville, Ky.

Asexual reproduction of the new *Euonymus* plant by softwood cuttings in a controlled environment in Louisville, Ky. since the spring of 2003, has shown that the unique features of this new *Euonymus* plant are stable and reproduced true to type in successive generations.

SUMMARY OF THE INVENTION

Plants of the new *Euonymus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Hayman'. These characteristics in combination distinguish 'Hayman' as a new and distinct cultivar of *Euonymus:*

1. Compact, upright and mounding plant habit.
2. Relatively rapid growth rate.
3. Freely branching habit.
4. Relatively small and fine leaves.
5. Attractive autumn leaf color.

Plants of the new *Euonymus* differ primarily from plants of the female parent, 'Rudy Haag', in the following characteristics:

1. Plants of the new *Euonymus* are larger than plants of 'Rudy Haag'.
2. Plants of the new *Euonymus* grow faster than plants of 'Rudy Haag'.
3. Plants of the new *Euonymus* are more freely branching than plants of 'Rudy Haag'.
4. Leaves of plants of the new *Euonymus* are smaller and finer than leaves of plants of 'Rudy Haag'.
5. Plants of the new *Euonymus* and 'Rudy Haag' differ in autumn leaf color.

Plants of the new *Euonymus* can be compared to plants of *Euonymus alata* 'Compacta', not patented. Plants of the new *Euonymus* differ from plants of 'Compacta' in the following characteristics:

1. Plants of the new *Euonymus* are much smaller than plants of 'Compacta'.
2. Plants of the new *Euonymus* are more freely branching than plants of 'Compacta'.
3. Leaves of plants of the new *Euonymus* are smaller and finer than leaves of plants of 'Compacta'.
4. Plants of the new *Euonymus* and 'Compacta' differ in autumn leaf color.

BRIEF DESCRIPTION OF THE PHOTOGRAPHS

The accompanying colored photographs illustrate the overall appearance of the new *Euonymus* plant, showing the colors as true as it is reasonably possible to obtain in colored reproductions of this type. Colors in the photographs may differ slightly from the color values cited in the detailed botanical description which accurately describe the colors of the new *Euonymus* plant.

The photograph on the first sheet comprises a side perspective view of a typical plant of 'Hayman' grown in an outdoor nursery.

The photograph on the second sheet is a close-up view of a typical plant of 'Hayman' grown in an outdoor nursery during the autumn.

DETAILED BOTANICAL DESCRIPTION

The aforementioned photographs and following observations, measurements and values describe plants grown in Grand Haven, Mich., under commercial practice in containers in an outdoor nursery. Plants were 3.5 years old when the photographs and description were taken. In the following description, color references are made to The Royal Horticultural Society Colour Chart, 2001 Edition, except where general terms of ordinary dictionary significance are used.

Botanical classification: *Euonymus alata* 'Hayman'.

Parentage:

*Female, or seed, parent.*—*Euonymus alata* 'Rudy Haag', not patented.

*Male, or pollen, parent.*—Unknown selection of *Euonymus alata,* not patented.

Propagation:

*Type.*—By softwood cuttings.

*Time to initiate roots.*—About 15 days at temperatures of 25° C.

*Time to produce a rooted young plant.*—About 65 days at temperatures of 25° C.

*Root description.*—Medium in thickness, fibrous; brown and creamy white in color.

*Rooting habit.*—Freely branching; dense.

Plant description:

*Plant form/habit.*—Compact, upright and mounding plant habit; relatively rapid growth rate; freely branching habit, about 46 lateral branches per plant; pinching enhances lateral branch development; dense and bushy appearance; vigorous growth habit.

*Plant height.*—About 54 cm.

*Plant width* (*spread*).—About 30 cm.

*Lateral branches.*—Length: About 15 cm. Internode length: About 2 cm. Strength: Strong. Aspect: About 20° to 30° from main stem axis. Texture: Smooth, glabrous; four-ridged. Color, developing: Close to 165A. Color, developed: Close to 137A.

Foliage description:

*Arrangement.*—Alternate to whorled, simple.

*Length.*—About 4 cm.

*Width.*—About 1.5 cm.

*Shape.*—Lanceolate.

*Apex.*—Acuminate to acute.

*Base.*—Obtuse.

*Margin.*—Serrulate.

*Texture, upper and lower surfaces.*—Smooth, glabrous.

*Venation pattern.*—Pinnate.

*Color.*—Developing leaves, upper surface: Close to 141A. Developing leaves, lower surface: Close to 144C. Fully developed leaves, upper surface: Close to 137A; venation, close to 137C; in the autumn, color becomes closer to 53B to 53D. Fully developed leaves, lower surface: Close to 137D; venation, close to 138B.

*Petiole.*—Length: About 3 mm. Diameter: About 1 mm. Texture, upper and lower surfaces: Smooth, glabrous. Color, upper and lower surfaces: Close to 138B.

Flower description: Flower initiation and development has not been observed on plants of the new *Euonymus.*

Disease/pest resistance: Plants of the new *Euonymus* have not been noted to be resistant to pathogens and pests common to *Euonymus.*

Temperature tolerance: Plants of the new *Euonymus* have been observed to tolerate temperatures from about −25° C. to about 37° C.

It is claimed:

1. A new and distinct *Euonymus* plant named 'Hayman' as illustrated and described.

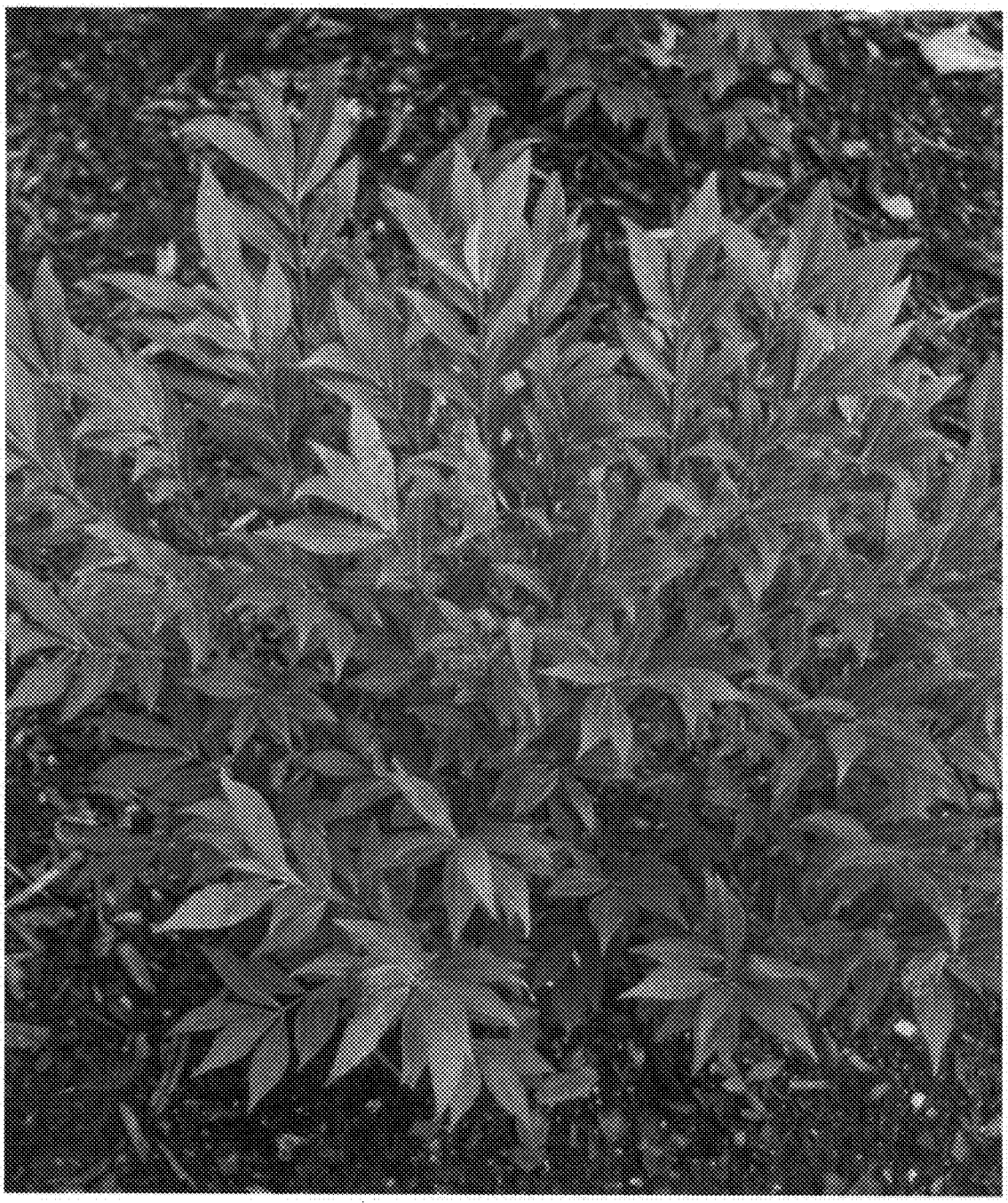

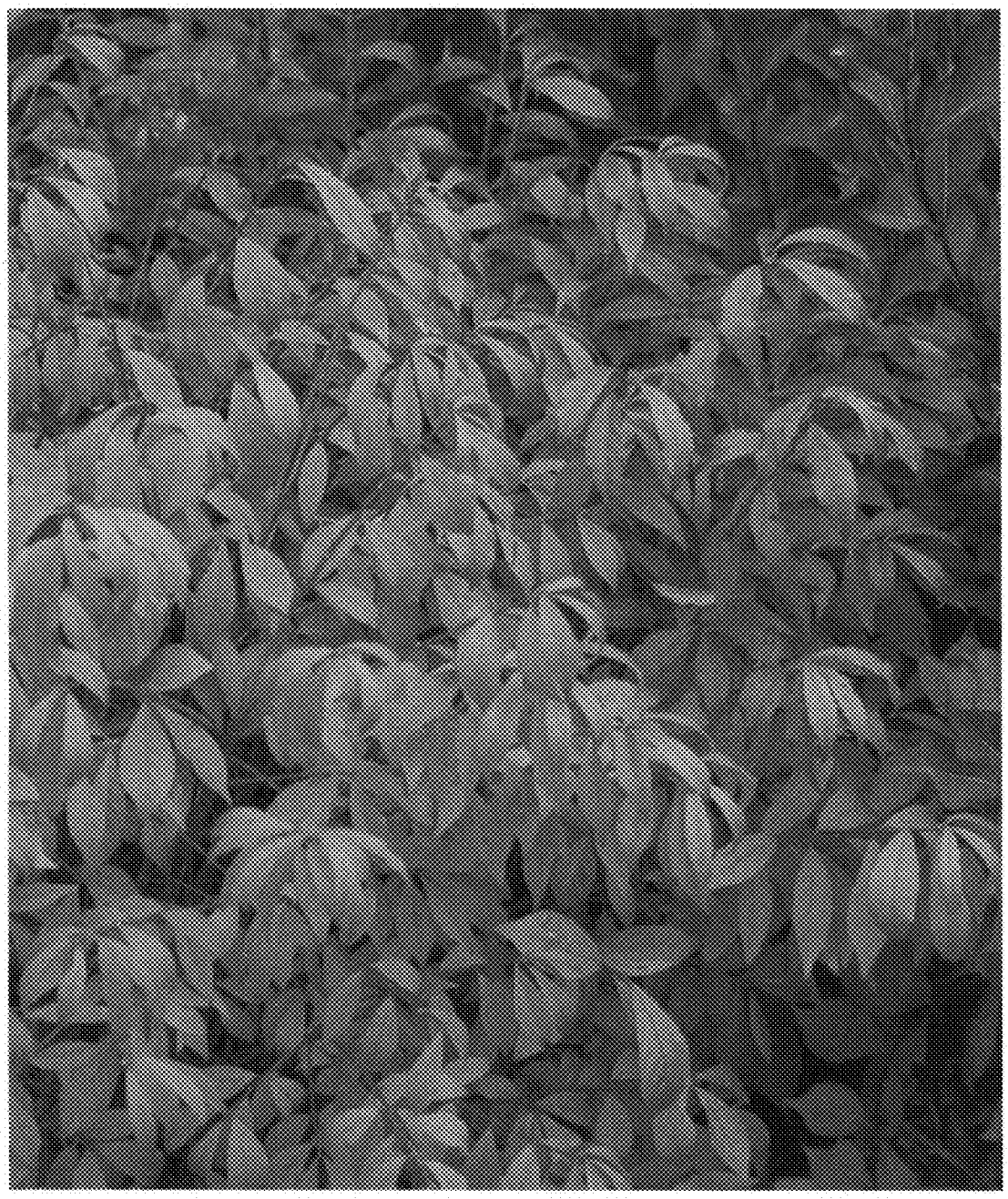

* * * * *